United States Patent [19]

Sawicki et al.

[11] Patent Number: 5,093,513

[45] Date of Patent: * Mar. 3, 1992

[54] PROCESS FOR OXYCARBONYLATION OF LOWER ALKANOLS

[75] Inventors: Robert A. Sawicki, Wappingers Falls; Harry Chafetz, Glenham, both of N.Y.

[73] Assignee: Texaco Inc., White Plains, N.Y.

[*] Notice: The portion of the term of this patent subsequent to Aug. 25, 2004 has been disclaimed.

[21] Appl. No.: 146,922

[22] Filed: Jan. 22, 1988

Related U.S. Application Data

[62] Division of Ser. No. 505,598, Jun. 20, 1983, abandoned.

[51] Int. Cl.$^5$ .................... C07C 68/00; C07C 69/96
[52] U.S. Cl. .................... 558/277; 502/155; 502/158; 556/413; 556/418; 556/419
[58] Field of Search .......................... 558/277

[56] References Cited

U.S. PATENT DOCUMENTS

| | | | |
|---|---|---|---|
| 3,980,690 | 9/1976 | Cpriani et al. | 558/277 |
| 3,994,960 | 11/1976 | Yamazaki et al. | 558/277 |
| 4,218,391 | 8/1980 | Romano et al. | 558/277 |
| 4,318,862 | 3/1982 | Romano et al. | 558/277 |
| 4,689,422 | 8/1987 | Sawicki et al. | 558/277 |

Primary Examiner—Vivian Garner
Attorney, Agent, or Firm—Robert A. Kulason; James J. O'Loughlin; Carl G. Seutter

[57] ABSTRACT

A lower alkanol, such as methanol is oxycarbonylated with carbon monoxide and oxygen to yield e.g. dimethyl carbonate at 50° C.–125° C. and 300–1500 psig in the presence of as catalyst, a functionalized inorganic oxide substrate (such as silica gel) typically bearing on the surface thereof a ligand of ethyl formate and 3-aminopropyl triethoxy silane—which has been reacted with a metal salt such as $CuCl_2$.

13 Claims, No Drawings

PROCESS FOR OXYCARBONYLATION OF LOWER ALKANOLS

This is a division of application Ser. No. 505,598 filed June 20, 1983, now abandoned.

FIELD OF THE INVENTION

This invention relates to novel ligand catalyst systems. More particularly it relates to complexed metals bonded to inorganic oxide supports.

BACKGROUND OF THE INVENTION

The art of immobilizing various materials on solid supports permits attainment of the advantages of both homogeneous catalysts and heterogeneous catalysts. Illustrative of prior art directed to this art are (i) R. B. Merrifield J. Am. Chem. Soc. 85 2149 (1963); (ii) U.S. Pat. No. 3,709,855; (iii) D. D. Whitehurst, CHEMTECH 44 (1980), (iv) P. Tundo et al J. Am. Chem. Soc. 101, 6606 (1979); (v) U.S. Pat. No. 3,980,583; etc.

It is an object of this invention to provide a novel ligand catalyst system. Other objects will be apparent to those skilled in the art.

STATEMENT OF THE INVENTION

In accordance with certain of its aspects, this invention is directed to a process which comprises reacting in liquid phase:
(i) organometallic amine $$(RO)_{3-n}Si \underset{R'''_n}{\overset{R'NHR''}{\diagup\diagdown}}$$

wherein R and R'' are hydrogen, alkyl, alkaryl, aralkyl, cycloalkyl, or aryl, R' is alkylene, alkarylene, aralkylene, cycloalkylene, or arylene, R''' is alkyl, aryl, or cycloalkyl, and n is an integer 0, 1, or 2, with
(ii) a carbonyl-containing organic compound selected from the group consisting of carboxylic acids, carboxylic acid esters, ketones, aldehydes, and acid anhydrides thereby forming product $$(RO)_{3-n}Si \underset{R'''_n}{\overset{R'NHR''}{\diagup\diagdown}} \quad (G)$$

wherein G is a residue of said carbonyl-containing organic compound bonded to said nitrogen atom N through a carbon atom.

In accordance with certain of its other aspects, this invention is directed to a novel catalyst comprising
(i) an inert oxide substrate bearing on the surface thereof
(ii) at least one residue $$-Si \underset{R'''_n}{\overset{R'NHR''}{\diagup\diagdown}} \quad (G)$$

wherein
R'' is hydrogen, alkyl, alkaryl, aralkyl, cycloalkyl, or aryl;
R' is alkylene, alkarylene, aralkylene, cycloalkylene, or arylene;
R''' is alkyl, alkaryl, aralkyl, cycloalkyl or aryl;
n is an integer 0, 1, or 2,
G is a residue of a carbonyl-containing organic compound; and
bonded thereto a metal salt.

DESCRIPTION OF THE INVENTION

The organometal compound which may be used to form the ligands of this invention may be characterized by the formula $$(RO)_{3-n}Si \underset{R'''_n}{\overset{(R'NHR'')}{\diagup\diagdown}}$$

wherein R and R'' are selected from the group consisting of hydrogen, alkyl, alkaryl, aralkyl, cycloalkyl, and aryl, R''' is alkyl, aryl, or cycloalkyl, R' is a hydrocarbon selected from the group consisting of alkylene, alkarylene, aralkylene, cycloalkylene, and arylene; and n is an integer 0, 1, or 2.

When R or R'' or R''' is alkyl, it may typically be methyl, ethyl, n-propyl, iso-propyl, n-butyl, i-butyl, sec-butyl, amyl, octyl, decyl, octadecyl, etc. When R or R'', or R''' is aralkyl, it may typically be benzyl, beta-phenylethyl, etc. When R or R'' or R''' is cycloalkyl, it may typically be cyclohexyl, cycloheptyl, cyclooctyl, 2-methylcycloheptyl, 3-butylcyclohexyl, 3-methylcyclohexyl, etc. When R or R'' or R''' is aryl, it may typically be phenyl, naphthyl, etc. when R or R'' is alkaryl, it may typically be tolyl, xylyl, etc. R or R'' or R''' may be inertly substituted i.e. it may bear a non-reactive substituent such as alkyl, aryl, cycloalkyl, etc. The preferred groups may be lower alkyl, i.e. $C_1$-$C_{10}$ alkyl, groups (or groups derived therefrom) including e.g. methyl, ethyl, n-propyl, i-propyl, butyls, amyls, hexyls, octyls, decyls, etc. R may preferably be ethyl; R' may preferably be propylene $(CH_2)_3$.

Illustrative organometal silicon compounds which may be employed may be the following:

TABLE 3-aminopropyl triethoxy silane
N-(2-aminoethyl-3-aminopropyl) trimethoxy silane
3-aminopropyl trimethoxy silane The preferred compound may be 3-aminopropyl triethoxy silane in which R is ethyl, R' is propylene $(CH_2)_3$, and n is zero. These compounds may be available commercially or they may be readily prepared.

The carbonyl-containing organic compounds, which may be reacted with the organometallic compounds in practice of the process of this invention, may be typified by those containing the following functionality: carboxylic acid, carboxylic acid ester, ketone, aldehyde, acid anhydride, etc.

Illustrative carbonyl-containing organic compounds which may be employed may be the following:

TABLE acetic acid
benzoic acid

TABLE ethyl formate
ethyl acetoacetate

TABLE 2,4-pentanedione
2,6-hexanedione

TABLE salicylaldehyde
acetaldehyde

TABLE succinic anhydride
phthalic anhydride

The reaction between the organometal compound and the carbonyl-containing organic compounds in practice of the process of this invention may be carried out by use of 0.1–10 moles, say 1 mole of carbonyl-containing compound per mole of organometal silcon compound.

The reaction may be carried out in the presence of solvent if desired, typically lower alcohols such as ethanol or hydrocarbons such as hexane. Preferrably reaction is carried out in liquid phase at 0° C.–150° C., say 0° C. and atmospheric pressure by adding one reactant, typically the organometal compound, slowly with agitation over 5–120 minutes to the carbonyl-containing organic compound.

After addition is complete, the reaction mixture is heated to reflux, typically 50° C.–150° C., say 70° C. for 1–24 hours, say 3 hours. At the conclusion of the reaction, the solvent may be recovered by distillation and the excess of carbonyl-containing compound may also be similarly removed.

The ligands so prepared may be recovered as high boiling liquids. Typical of the reactions may be the following.

$$(EtO)_3Si(CH_2)_3NH_2 + H\overset{O}{\overset{\|}{C}}-OEt \longrightarrow$$

$$(EtO)_3Si(CH_2)_3NHCHO + EtOH$$

Illustrative products which may be prepared include the following:

TABLE

A. $(EtO)_3Si(CH_2)_3NHCHO$

B. $(MeO)_3Si(CH_2)_3NCH_2CH_2NHCHO$
$\qquad\qquad\qquad\quad|$
$\qquad\qquad\qquad\;\,CHO$ C. 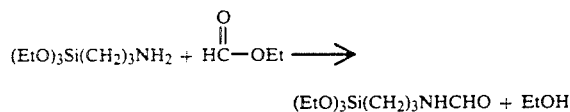

D. $(EtO)_3Si(CH_2)_3NHC=CHC-CH_3$
$\qquad\qquad\qquad\qquad\;|\quad\;\;\|$
$\qquad\qquad\qquad\quad\;CH_3\;\;O$ E. $(EtO)_3Si(CH_2)_3N=CH$ 

TABLE-continued

F. $(EtO)_3Si(CH_2)_3NH\overset{O}{\overset{\|}{C}}CH_2CH_2COOH$

It is a feature of the process of this invention that it is possible to bond these ligands to the surface of inorganic oxide substrates or supports, which are characterized by the presence of pendent surface hydroxyl groups.

The charge solid inorganic oxides which may be used as substrates in practice of the process of this invention may include a wide variety of porous refractory oxides typified by those which may commonly be used as inert catalyst supports. Although they may be used in impure form or as mixtures, more consistent results may be attained by the use of one species of pure porous refractory metal oxide. Illustrative of the porous refractory solid inorganic metal (including metalloid) oxides may be oxides of boron, magnesium, aluminum, silicon, phosphorus, calcium, titanium, vanadium, chromium, manganese, iron, cobalt, nickel, copper, zinc, arsenic, cadmium, barium, etc. It will be apparent that certain oxides typified by those of sodium may be too active under reaction conditions and may not be employed. Others may be too expensive. The preferred solid refractory oxides are those commonly referred to as inert and which have heretofore been proposed for use as catalyst supports. Most preferred are aluminum oxide ($Al_2O_3$) and silicon dioxide ($SiO_2$). Complex oxides may be employed viz: silica-magnesia; etc. It will be apparent that silicon is frequently referred to as a metalloid; but it is intended to be embraced within the term "metal" as used herein; and in fact silicon dioxide is a preferred charge solid inorganic porous refractory metal oxide. A preferred form of silica is that referred to as silica gel.

It is also possible to use as substrates refractory oxides wich are crystalline aluminosilicates including synthetic zeolites typified by zeolites X, Y, ZSM-4, ZSM-5, ZSM-11, ZSM-21, etc. as well as naturally occurring zeolites such as erionite, faujasite, mordenite, etc.

The surface of the charge porous refractory inorganic metal oxide bears a plurality of pendant hydroxyl groups. Although it may be possible to use the porous refractory oxides as they are obtained, it is preferred to pretreat them preferably by heating to drive off adsorbed water, at 50° C.–450° C., say 200° C. for 1–24 hours, say 6 hours at atmospheric pressure. In the case of silica, it may alternatively be desirable to pretreat by reaction in aqueous medium in liquid phase with a Bronsted acid, typically at 25° C.–100° C., say 100° C. for 1–24 hours, say 4 hours. Illustrative Bronsted acids include hydrogen halides, preferably hydrogen chloride.

During this pretreatment, it appears that additional hydroxyl groups may be made available for reaction. Pretreatment is not necessary however.

In practice of the preferred mode of carrying out the process of this invention, the ligand which has been formed from the organometallic silicon compound and the carbonyl-containing organic compound is reacted with a metal salt.

Typical metal salts may be salts of metals of Group IB (Ag or Au or preferably Cu) or of Group VIII (Fe, Co, Ni, Ru, Rh, Pd, Os, Ir, Pt).

The metal salts may already have ligands attached to them—ionic, neutral, or mixed—typified by ammonia, phosphine, carbon monoxide, olefins, etc. The anion may preferably be halide (fluoride, chloride, bromide, or iodide), halogen-like (cyanide, cyanate, thiocyanate) etc, or others typified by nitrate, sulfate, phosphate, sulfide, carbonate, or carboxylate, (either acidic, basic, or neutral).

Illustrative salts may include (the first four being preferred):

TABLE $Cu_2Cl_2$
$CuCl_2$
$FeCl_2$
$PdCl_2$
$NiCl_2$
$CuCl\ (OCH_3)$
$CuBr_2$
$CuSO_4$
$RhCl_3$
$RuI_3$

Reaction, in the preferred embodiment, between the metal salt and the ligand is preferably effected by addition of one mole of the former (dissolved in solvent such as absolute ethanol) to 0.01-10 moles, say 1 mole of the latter (also dissolved in solvent such as absolute ethanol). Reaction is effected at $-50°$ C. to $50°$ C., say $20°$ C. and preferably atmospheric pressure over 5-180 minutes, say 60 minutes.

At the end of this reaction period, there is added hydrocarbon solvent (preferably toluene) in amount of 50-10,000 ml, say 500 ml per mole of ligand and there is also added inorganic oxide in amount of 1-5000 g, say 700 g per mole of ligand.

The mixture is heated to reflux at $50°$ C.-$150°$ C., say $100°$ C. for 5-600 minutes, say 240 minutes during which distillate is removed and replaced with an equivalent amount of e.g. toluene. The procedure is repeated twice during which total time of reflux of 4 hours, the toluene-alcohol azeotrope is removed to drive the reaction to completion.

The mixture is cooled to ambient temperature of $20°$ C.-$30°$ C., say $25°$ C. and filtered - the solid being washed with fresh toluene and then with ethanol. Product after drying at room temperature under vacuum is typically a colored powder obtained in yield of 80-100%, say 90% based on charged reactants.

In practice of the process of this invention, it is possible to form the desired product by any of the following routes:

(i) reacting the organometal amine A with the carbonyl-compound B to form the ligand, then reacting this with the support C to form the immobilized ligand, and then reacting with the metal salt D to form the immobilized metal complex—viz ABCD;

(ii) reacting the organometal amine A with the carbonyl-compound B and the metal salt D (in two steps or preferably one step) to form a preformed complex and then reacting with the support C to form the immobilized metal complex—viz ABDC;

(iii) adding all the ingredients to the reaction vessel simultaneously;

(iv) reacting the organometal amine A with the support C, then reacting with the carbonyl compound B, followed by reacting with the metal salt D - viz ACBD.

Other equivalent variants will be apparent to those skilled in the art.

Although the order of addition of the several components may be modified, it is preferred that the ligand be formed first by reaction of organometal compound A and carbonyl-containing organic compound B, then this be reacted with metal salt D and then the solid oxide C be added, e.g., the ABDC sequence.

The product of this invention according to certain of its aspects may be a complex of a metal salt with an inorganic oxide bearing immobilized thereon a ligand of a carbonyl-containing organic compound and an alkoxy primary or secondary amine of an organometallic-bond-forming atom.

Typical of these products may be the following:

TABLE

| Carbonyl-Ctg Compound | Amine | Metal Salt | Inorganic Oxide |
|---|---|---|---|
| Ethyl Formate | 3-aminopropyl triethoxy silane | $CuCl_2$ | $SiO_2$ |
| Ethyl Formate | N-(2-aminoethyl-3-aminopropyl) trimethoxy silane | $FeCl_2$ | $SiO_2$ |
| Ethyl Acetoacetate | 3-aminopropyl-triethoxy silane | $PdCl_2$ | $SiO_2$ |
| 2,4-pentanedione | 3-aminopropyl-triethoxy silane | $NiCl_2$ | $SiO_2$ |
| salicylaldehyde | 3-aminopropyl-triethoxy silane | $CuCl_2$ | $Al_2O_3$ |
| succinic anhydride | 3-aminopropyl-triethoxy silane | $CuCl_2$ | $TiO_2$ |
| Ethyl Formate | N-(2-amino ethyl-3 aminopropyl) trimethoxy silane | $CuCl\ (OCH_3)$ | $SiO_2$ |

It is a feature of the process of this invention that these novel products may be used as catalysts for various reactions depending upon the specific composition. They may be found to be useful in oxidative carbonylation reactions typified by the preparation of dimethyl carbonate from methanol. A preferred embodiment may be that last set forth in the above table.

In a typical oxidative carbonylation, the charge, e.g., methanol may be added to a reaction vessel with the catalyst and, after flushing with carbon monoxide, pressured to 100-5000 psig, say 1000 psig with monoxide at $0°$ C.-$50°$ C., say $25°$ C.

The reaction mixture may be maintained at $50°$ C.-$125°$ C., say $100°$ C. for 1-24 hours, say 8 hours with agitation. After cooling to ambient temperature, the reaction mixture, analyzed by gas chromatography (using isooctane as an internal standard), is found to contain dimethyl carbonate in yield (based on methanol) of 18%-36%, say 36% using $CuCl_2$.

In the absence of ligands or supports, $CuCl_2$ gives yields of dimethyl carbonate of ca 12% or less.

It is a feature of the process of this invention that yield of product in the oxidative carbonylation reaction may be substantially increased if the metal salt, employed in a lower valence state, is oxidized to a higher valence state in the presence of the charge which is to be oxidatively carbonylated.

In one preferred embodiment, the catalyst may be formed from cuprous chloride (e.g. an immobilized cuprous chloride complex of silicon dioxide bearing immobilized thereon a ligand of ethyl formate and N-(2-aminoethyl-3-aminopropyl) trimethoxy silane).

This lower valent catalyst may be added to the reaction vessel together with solvent (preferably methanol). The cuprous ion may be oxidized as by passing dry air through the reaction mixture at 0° C.-50° C., say 45° C. for 1-24 hours say 6 hours. The oxidized catalyst is then flushed with carbon monoxide and pressured to 100-2000 psig, say 1000 psig at ambient temperature and heated to 50° C.-125° C., say 100° C. for 1-24 hours, say 8 hours. After cooling, analysis by gas chromatogrophy (using isooctane as an internal standard) showed attainment of a yield, based on copper salt charged, of 33%-69%, say 69%.

It is a particular feature of the process of this invention that it may be carried out in a continuous manner. In this continuous process, the catalyst may for example be a complex (prepared from cuprous chloride $Cu_2Cl_2$, with silicon dioxide on which is immobilized a ligand of ethyl formate and 3-aminopropyl triethoxy silane) in the form of a packed bed of particles of about 5-6 mm diameter.

Air may be passed upwardly through the bed. Reaction is carried out at 50° C.-125° C., say 90° C. and 300-1500 psig, say 600 psig.

As these compounds pass through the catalyst bed, the carbon monoxide and the methanol react in liquid phase to form dimethyl carbonate in the presence of oxygen:

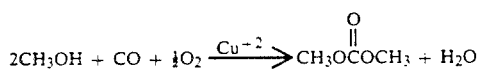

It also appears that the metal salt (e.g., copper (I) chloride) may participate in the reaction as follows (L* represents the supported ligand):

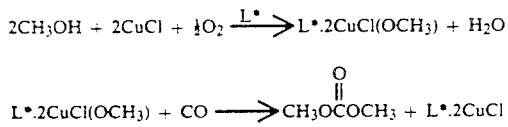

Product withdrawn from the reactor includes dimethyl carbonate and water. Anhydrous dimethyl carbonate may be obtained by distillation.

Dimethyl carbonate may be employed as an additive to hydrocarbon fuels including gasolines; and it also finds use as an intermediate in many chemical reactions wherein it may replace phosgene.

DESCRIPTION OF SPECIFIC EMBODIMENTS

Practice of the process of this invention will be apparent to those skilled in the art from the following examples.

All reactions were carried out using reagent grade materials with no prior purification. The catalysts were routinely prepared under an inert atmosphere.

Catalyst Preparation—Ligand Formation

Example I

Amide Ligand. Reaction of 3-Aminopropyltriethoxysilane with ethyl formate.

A reaction flask containing 220 ml (2.73 mol) ethyl formate was cooled to 0° C. in an ice bath; and 3-aminopropyltriethoxy silane (120 g, 0.54 mol) was added slowly with stirring. After complete addition the mixture was heated at reflux for ten hours. The excess ethyl formate was stripped from the product on a rotary evaporator at room temperature under vacuum to afford 147 g of an orange liquid. Infrared (IR) and nuclear magnetic resonance (NMR) spectroscopy were consistent with the proposed amide ligand structure.

Example II

Diamide Ligand. Reaction of N-(2-aminoethyl-3-aminopropyl) trimethoxysilane with ethyl formate.

To a flask containing 150 ml (1.86 mol) ethyl formate cooled as in Example I was added 30 g (0.14 mol) N-(2-aminoethyl-3-aminopropyl) trimethoxysilane. After ten hours at reflux, the excess ethyl formate was removed by stripping as in Example I to yield 39 g of a yellow liquid. Both IR and NMR analyses were consistent with the proposed structure.

Example III

Enaminone Ligand. Reaction of 3-Aminopropyltriethoxy silane with ethyl acetoacetate.

Into a flask containing a stirrer, addition funnel and Dean Stark trap with reflux condenser was added 15 g (0.12 mol) ethyl acetoacetate, 25 ml absolute ethanol, and 150 ml heptane. While stirring, 25 g (0.11 mol) 3-aminopropyltriethoxy silane was added slowly at room temperature. After complete addition, the mixture was heated at reflux for 3 hours with continuous removal of the bottom layer that was collected in the Dean-Stark trap (19 ml, calc. 2.8 ml water, 0.16 mol). The resulting mixture was stripped of residual solvent at 50° C. under vacuum to afford 37 g of a pale yellow liquid. Both IR and NMR analyses were consistent with the proposal structure.

Example IV

Enaminone Ligand. Reaction of 3-aminopropyltriethoxy silane with 2,4 Pentanedione.

Into a flask fitted as in Example III was added 11 g (0.11 mol) 2,4-pentanedione, 25 ml absolute ethanol, and 150 ml heptane. While stirring, 25 g (0.11 mol) 3-aminopropyltriethoxysilane was added slowly at room temperature. The mixture was heated to reflux for 3 hours removing 13 ml of the bottom azeotropic layer (calc. 2 ml water, 0.11 mol). Stripping at 50° C. under vacuum yielded 31 g of a brown liquid. Both IR and NMR analyses were consistent with the proposed structure.

Example V

Schiff Base Ligand. Reaction of 3-aminopropyltriethoxy silane with salicylaldehyde.

Into a flask fitted as in Example III was added 14 g (0.11 mol) salicylaldehyde, 25 ml absolute ethanol, and 150 ml heptane. While stirring, 25 g (0.11 mol) 3-aminopropyltriethoxysilane was added slowly at room temperature. The mixture was heated to reflux for 3 hours removing 16 ml of the bottom azeotropic layer (calc. 2.4 ml water, 0.13 mol). Stripping at 50° C. under vacuum yielded 36 g of a brown liquid. Both IR and NMR analyses were consistent with the proposed structure.

Example VI

Amide-Acid Ligand. Reaction of 3-aminopropyltriethoxy silane with succinic anhydride.

Into a flask fitted as in Example III was added 11 g (0.11 mol) succinic anhydride, 25 ml. absolute ethanol, and 150 ml heptane. While stirring, 25 g (0.11 mol) 3-aminopropyltriethoxy silane was added slowly at room temperature. The mixture was heated at reflux for 3 hours with no formation of a lower azeotropic layer. Stripping at 50° C. under vacuum afforded 39 g of a viscous yellow liquid. Both IR and NMR analyses were consistent with the proposed structure.

Catalyst Preparation—Metal Complexation

Example VII

Copper Salt. Reaction of Cupric Chloride with product of Example I and attachment to Silica Gel.

Into a flask fitted with an addition funnel, Dean Stark trap and stirrer was added 6.8 g (0.027 mol) of the product of Example I and 25 ml absolute ethanol. Cupric chloride (2.1 g, 0.016 mol) was dissolved in 25 ml absolute ethanol and this solution added slowly to the pot at room temperature. After addition the mixture was stirred one hour at room temperature. Toluene (150 ml) was added along with 20 g silica gel. The solution was heated at reflux for one hour and 25 ml distillate was removed. Fresh toluene (25 ml) was added to the pot and the procedure repeated 3 more times (Total-4 hours reflux, 100 ml distillate removed, 100 ml fresh toluene added). After cooling, the mixture was filtered and the solid washed slowly with fresh toluene (50 ml) and then with ethanol (50 ml). The solid was then dried at room temperature under vacuum to yield a yellow powder, 26 g, which contained 7.71 percent carbon, 1.38 percent nitrogen and 2.27 percent copper.

Example VIII

Iron Salt. Reaction of Ferrous Chloride with product of Example I and attachment to Silica Gel.

The procedure of Example VII was followed with 2.0 g (0.06 mol) ferrous chloride ($FeCl_2$). Drying at room temperature under vacuum afforded a light orange powder (28.8 g) containing 5.10 percent carbon, 1.26 percent nitrogen, and 2.4 percent iron.

Example IX

Palladium Salt. Reaction of Palladium Chloride with product of Example I and attachment to Silica Gel.

The procedure of Example VII was followed with 2.8 g (0.016 mol) palladium chloride ($PdCl_2$). Drying at room temperature under vacuum afforded a dark brown powder (27.6 g) containing 4.96 percent carbon, 1.32 percent nitrogen, and 2.3 percent palladium.

Example X

Nickel Salt. Reaction of Nickel Chloride with product of Example I and attachment to Silica gel.

The procedure of Example VII was followed with 3.7 g (0.016 mol) nickel chloride hexahydrate ($NiCl_2.6-H_2O$). Drying at room temperature under vacuum afforded a light green powder (31.1 g) containing 5.09 percent carbon, 1.24 percent nitrogen, and 2.5 percent nickel.

Example XI

Copper Salt. Reaction of Cupric Chloride with product of Example II and attachment to silica gel.

The procedure of Example VII was followed using 34 g (0.12 mol) catalyst from Example II, 75 ml ethanol, 100 g silica gel and 21 g (0.16 mol) cupric chloride. Drying at room temperature under vacuum afforded 152 g of a gold powder containing 7.91 percent carbon, 1.93 percent nitrogen, and 5.2 percent copper.

Example XII

Copper Salt. Reaction of Cupric Chloride with product of Example III and attachment to silica gel.

Into a flask fitted as in Example VII was added 9 g (0.027 mol) of the product of Example III and 25 ml absolute ethanol. A mixture of cupric chloride (3.6 g, 0.027 mol) in 25 ml absolute ethanol was added slowly over 30 minutes. After stirring at room temperature for one hour, toluene (150 ml) and silica gel (20 g) were added and the procedure followed as in Example VII. Drying at room temperature under vacuum afforded 26 g of a dark green powder containing 6.27 percent carbon, 1.0 percent nitrogen and 5.0 percent copper.

Example XIII

Copper Salt. Reaction of Cupric Chloride with product of Example IV and attachment to Silica Gel.

Into a flask fitted as in Example VII was added 8.2 g (0.027 mol) Example IV and 25 ml absolute ethanol. Cupric chloride (3.6 g, 0.027 mol) in ethanol (25 ml) was added slowly and the procedure of Example VII was followed using toluene and silica gel (20 g). Drying at room temperature under vacuum afforded 26 g of a dark gold powder containing 6.99 percent carbon 0.96 percent nitrogen, and 4.5 percent copper.

Example XIV

Copper Salt. Reaction of Cupric Chloride with product of Example V and attachment to silica gel.

Into a flask fitted as in Example VII containing 8.8 g (0.027 mol) Example V and 25 ml ethanol was added 3.6 g (0.027 mol) cupric chloride in 25 ml ethanol. The procedure of Example VII was followed using toluene and silica gel (20 g). Drying at room temperature under vacuum yielded 27 g of a brown powder containing 9.21 percent carbon, 1.18 percent nitrogen, and 4.9 percent copper.

Example XV

Copper Salt. Reaction of Cupric Chloride with product of Example VI and attachment to silica gel.

Into a flask fitted as in Example VII containing 8.6 g (0.027 mol) Example VI and 25 ml ethanol was added 3.6 g (0.027 mol) cupric chloride in 25 ml ethanol. The procedure of Example VII was followed using toluene and silica gel (20 g). Drying at room temperature under vacuum afforded 25 g of a gold powder containing 8.58 percent carbon, 1.13 percent nitrogen, and 2.1 percent copper.

Example XVI

Copper Salt. Reaction of Cupric Chloride with product of Example IV and attachment to titanium dioxide.

The procedure of Example XIII was followed using 20 g titanium dioxide instead of silica gel. The dried light brown powder (22 g) contained 2.81 percent carbon, 0.60 percent nitrogen and 4.2 percent copper.

Example XVII

Copper Salt. Reaction of Cupric Chloride with product of Example IV and attachment to alumina.

The procedure of Example XIII was followed using 20 g alumina instead of silica gel. The dried dark brown powder (26.5 g) contained 4.42 percent carbon, 0.86 percent nitrogen, and 5.9 percent copper.

Example XVIII

Amine Ligand. Reaction of 3-Aminopropyltriethoxysilane with silica gel.

Into a flask fitted with a stirrer and Dean Stark trap with reflux condenser was added 400 g silica gel, 1700 ml toluene, and 120 g (0.54 mol) 3-aminopropyltriethoxysilane. After heating to reflux for one hour 100 ml distillate was removed, and the mixture heated an additional two hours at reflux. A second 100 ml of distillate was removed, the pot heated an additional one hour at reflux and following filtration, the solid was washed with toluene (250 ml) and diethyl ether (250 ml). The white filter cake was dried at 75° C. under vacuum to yield 459 g of a white powder containing 4.91 percent carbon and 1.62 percent nitrogen.

Example XIX

Enaminone Ligand-Copper Salt. Reaction of 2,4-Pentanedione with product of Example XVI followed by complexation of cupric chloride.

Into a flask fitted as in Example XVIII was added 300 ml heptane, 40 g of Example XVI, and 6.4 g of acetylacetone (2,4-pentanedione). The solution was heated to reflux for three hours removing the bottom layer of the azeotrope (1.2 ml). After filtering, the solid was washed with heptane (50 ml) and diethyl ether (100 ml) and dried under vacuum at room temperature leaving 42 g of a pale yellow powder containing 10.85 percent carbon and 1.57 percent nitrogen. Twenty grams of this powder was then charged into a flask fitted with a stirrer and addition funnel and 75 ml ethanol added. Cupric chloride (4.4 g) was dissolved in 25 ml ethanol and this mixture added slowly to the pot at room temperature over 30 minutes. After stirring an additional 2 hours the solid was filtered, washed with fresh ethanol (50 ml) and dried at room temperature under vacuum affording 22 g of a brown powder containing 9.17 percent carbon, 1.43 percent nitrogen and 2.6 percent copper.

Example XX

Schiff Base Ligand-Copper Salt. Reaction of Salicylaldehyde with Example XVI followed by complexation of cupric chloride.

Same procedure was followed as in Example XIX using 7.8 g salicylaldehyde. Initial reaction yielded a bright yellow powder (44 g) containing 12.93 percent carbon and 1.47 percent nitrogen. Complexation with cupric chloride afforded a brown powder (22 g) containing 12.45 percent carbon, 1.43 percent nitrogen, and 3.3 percent copper.

Example XXI

Diamide Ligand-Copper Salt. Attachment of Example II to silica gel followed by complexation of cupric chloride.

Into a flask fitted with a stirrer and Dean Stark trap with reflux condenser was added 100 g silica gel, 500 ml toluene, and 30 g of Example II. The mixture was heated at reflux a total of four hours removing 25 ml of distillate at the end of one and three hours. After filtering, the white solid was washed with toluene (100 ml) and diethyl ether (100 ml). Drying under vacuum at 75° C. afforded 119 g of a white powder containing 7.55 percent carbon and 2.07 percent nitrogen. Into a flask containing 100 g of the above solid and 225 ml ethanol was added a solution of 20 g cupric chloride in 75 ml ethanol. After stirring at room temperature for two hours the mixture was filtered, the solid washed with fresh ethanol (100 ml), and dried at room temperature under vacuum to yield 110 g of a gold powder containing 6.28 percent carbon, 1.89 percent nitrogen, and 8.2 percent copper.

Catalyst Evaluation-Dimethyl Carbonate Production.

Example XXII

Oxidative Carbonylation of Methanol using the copper catalyst from Example VII.

Into a 1 liter Hastelloy autoclave fitted with a glass liner was added 125 ml methanol and 25 g of the product of Example VII. The reactor was flushed with carbon monoxide and pressurized to 1000 psig carbon monoxide at room temperature. The mixture was subsequently heated at 100° C. for eight (8) hours. After cooling the liquid was analyzed by gas chromatography using isooctane as an internal standard and shown to contain a 25% yield of dimethyl carbonate based on the copper salt charged.

Example XXIII

Oxidative Carbonylation of methanol using the copper catalyst from Example XI.

Same procedure as Example XXII using 25 g of the product Example XI. Gas chromatographic analyses indicated a 36% yield of dimethyl carbonate. This is the best yield obtained.

Example XXIV

Oxidative Carbonylation of methanol using the copper catalyst from Example XIX.

Same procedure as Example XXII using 25 g of the product of Example XXI. Gas chromatographic analysis indicated an 18% yield of dimethyl carbonate.

Example XXV

Oxidative Carbonylation of Methanol using the copper catalyst from Example XII.

Same procedure as Example XXII using 25 g of the product Example XII. Gas chromatographic analysis indicated a 25% yield of dimethyl carbonate.

Example XXVI

Oxidative Carbonylation of methanol using the copper catalyst from Example XIII.

Same procedure as Example XXII using 25 g of the product of Example XIII. Gas chromatographic analysis indicated a 25% yield of dimethyl carbonate.

Example XXVII

Oxidative Carbonylation of Methanol using the copper catalyst from Example XIV.

Same procedure as Example XXII using 25 g of the product of Example XIV. Gas chromatographic analysis indicated a 24% yield of dimethyl carbonate.

Example XXVIII

Oxidative carbonylation of methanol using the copper catalyst from Example XV.

Same procedure as Example XXII using 25 g of the product of Example XV. Gas chromatographic analysis indicated a 20% yield of dimethyl carbonate.

EXAMPLE XXIX

Reaction of product of Example II with Silica gel.

Into a 1 liter 3-neck flask fitted with a mechanical stirrer and Dean-Stark trap with reflux condenser was added 100 g silica gel, 400 ml toluene, and 34 g (0.12 mol) Example II. The mixture was heated at reflux for two hours and 50 ml distillate was collected and discarded. After an additional two hours at reflux and an additional 50 ml distillate removed the pot was cooled to room temperature. After filtering, the resulting white powder was Soxhlet extracted with methanol for 24 hours. Subsequent drying at 50° C. under vacuum afforded 117 g of a white powder containing 8.54 percent carbon and 2.37 percent nitrogen.

Example XXX

Oxidative carbonylation of methanol using cuprous chloride that was oxidized in the presence of methanol and the product of Example XXIX.

Into a 250 ml 3-neck flask fitted with a mechanical stirrer, air inlet tube, thermometer, and reflux condenser was added 25 g of the product Example XXIX, 5 g (0.05 mol) cuprous chloride and 150 ml methanol. Dry air was run through the heterogeneous mixture at 535 ml/min and the pot heated at 45° C. for 6 hours. The free flowing green powder containing the complexed copper salt was analyzed and found to contain 5.80 percent carbon, 1.35 percent nitrogen, and 8.3 percent copper. The resulting mixture was charged into a 1 liter Hastelloy autoclave fitted with a glass liner. The reactor was flushed with carbon monoxide and pressurized to 1000 psig carbon monoxide at room temperature. The pot was subsequently heated at 100° C. for eight (8) hours. After cooling, the liquid was analyzed by gas chromatography using isooctane as an internal standard and shown to contain a 69% yield of dimethyl carbonate based on the copper salt charge.

Although this invention has been illustrated by reference to specific embodiments, it will be apparent to those skilled in the art that various changes and modifications may be made which clearly fall within the scope of this invention.

We claim:

1. The process which comprises oxycarbonylating a lower alkanol with carbon monoxide and oxygen at 50° C.–125° C. and 300–1500 psig in the presence of, as catalyst, a functionalized inorganic oxide substrate composition comprising
   (i) an inert oxide substrate bearing on the surface thereof
   (ii) at least one residue -Si (R'R") (G) wherein
   R" is hydrogen, alkyl, aralkyl, cycloalkyl, or aryl;
   R' is alkylene, cycloalkylene, or arylene; and
   G is a residue of a carbonyl-containing organic compound; and
   bonded thereto a metal salt.

2. The process as claimed in claim 1 wherein said inorganic oxide is alumina or silica.

3. The process as claimed in claim 1 wherein R' is alkylene.

4. The process as claimed in claim 1 wherein R" is lower alkyl.

5. The process as claimed in claim 1 wherein said carbonyl-containing organic compound is a carboxylic acid ester.

6. The process as claimed in claim 1 wherein said carbonyl-containing organic compound is ethyl formate.

7. The process which comprises oxycarbonylating methanol with carbon monoxide and oxygen at 50° C.–125° C. and 300–1500 psig in the presence of, as catalyst, a functionalized inorganic oxide substrate composition comprising
   (i) an inert oxide substrate bearing on the surface thereof;
   (ii) at least one residue -Si (R'NR") (G) wherein
   R" is hydrogen, alkyl, aralkyl, cycloalkyl, or aryl;
   R' is alkylene, aralkylene, cycloalkylene, or arylene; and
   G is a residue of a carbonyl-containing organic compound; and
   bonded thereto cuprous chloride $CuCl_2$.

8. The process as claimed in claim 7 wherein said inorganic oxide is alumina or silica.

9. The process as claimed in claim 7 wherein R' is alkylene.

10. The process as claimed in claim 7 wherein R" is lower alkyl.

11. The process as claimed in claim 7 wherein said carbonyl-containing organic compound is a carboxylic acid ester.

12. The process as claimed in claim 7 wherein said carbonyl-containing organic compound is ethyl formate.

13. The process which comprises oxycarbonylating methanol with carbon monoxide and oxygen at 50° C.–125° C. and 300–1500 psig in the presence of, as catalyst, a functionalized inorganic oxide substrate composition comprising silica gel bearing on the surface thereof at least one residue $$-Si(CH_2CH_2CH_2NH)(G)$$

wherein
G is a residue of ethyl formate; and
bonded thereto cuprous chloride $Cu_2Cl_2$.

* * * * *